US010561582B2

(12) United States Patent
Wood

(10) Patent No.: US 10,561,582 B2
(45) Date of Patent: Feb. 18, 2020

(54) BABY BOTTLE SENSOR WITH CONTENT VOLUME SENSING AND CONTENT DEDUCTION LOGIC

(71) Applicant: Zak Wood, Santa Monica, CA (US)

(72) Inventor: Zak Wood, Santa Monica, CA (US)

(73) Assignee: Zak Wood, Santa Monica, CA (US)

(*) Notice: Subject to any disclaimer, the term of this patent is extended or adjusted under 35 U.S.C. 154(b) by 141 days.

(21) Appl. No.: 15/937,095

(22) Filed: Mar. 27, 2018

(65) Prior Publication Data

US 2019/0298615 A1    Oct. 3, 2019

(51) Int. Cl.
| A61J 9/06 | (2006.01) |
| A61J 9/00 | (2006.01) |
| G01F 23/26 | (2006.01) |
| A47G 19/00 | (2006.01) |
| G01N 11/02 | (2006.01) |
| A47G 19/22 | (2006.01) |

(52) U.S. Cl.
CPC ............ *A61J 9/06* (2013.01); *A47G 19/2227* (2013.01); *A61J 9/00* (2013.01); *G01F 23/266* (2013.01); *G01N 11/02* (2013.01); *A61J 2200/74* (2013.01); *A61J 2200/76* (2013.01)

(58) Field of Classification Search
CPC ...................................... A61J 9/00; A61J 9/06
See application file for complete search history.

(56) References Cited

U.S. PATENT DOCUMENTS

| 4,930,902 A | 6/1990 | Yata et al. |
| 6,033,367 A | 3/2000 | Goldfield |
| 6,109,100 A | 8/2000 | Buckley et al. |
| 6,542,848 B1 | 4/2003 | Neeser et al. |
| 6,606,905 B2 | 8/2003 | Carroll et al. |
| 6,751,525 B1 | 6/2004 | Crisp |
| 7,161,361 B2 | 1/2007 | Qu et al. |
| 7,553,234 B2 | 6/2009 | Walker et al. |
| 7,891,243 B2 | 2/2011 | Winkens |
| 7,896,835 B2 | 3/2011 | Dahan et al. |
| 8,284,068 B2 | 10/2012 | Johnson |
| 8,378,830 B2 | 2/2013 | Moran |
| 8,413,502 B2 | 4/2013 | Zemel et al. |
| 8,479,573 B2 | 7/2013 | Baily et al. |
| 8,482,416 B2 | 7/2013 | Krans et al. |
| 8,500,673 B2 | 8/2013 | Zanotti et al. |
| 8,931,340 B2 | 1/2015 | Wiederkind-Klein |
| 9,311,806 B2 | 4/2016 | Hazen et al. |
| 9,380,897 B2 | 7/2016 | Pfeiffer et al. |
| 9,382,107 B2 | 7/2016 | Pfeiffer et al. |
| 9,636,280 B1 | 5/2017 | Althallab |

(Continued)

FOREIGN PATENT DOCUMENTS

WO    WO-2016155024 A1 * 10/2016    ................ A61J 9/02

OTHER PUBLICATIONS

Abstract for CN-204995835-U; Jan. 2016; Guo, Xiaoliang.*

(Continued)

*Primary Examiner* — Daniel J Colilla

(57) ABSTRACT

A baby bottle sensor with content volume sensing and content deduction logic is attachable to a baby bottle. The sensor measures a volume of fluid in the baby bottle and uses programmed logic to deduce whether formula or some other fluid is being fed. Collected data is stored and reported to a paired Bluetooth device.

20 Claims, 19 Drawing Sheets

(56) References Cited

U.S. PATENT DOCUMENTS

| | | |
|---|---|---|
| 9,713,577 B2 | 7/2017 | LePine |
| 9,756,873 B2 | 9/2017 | Bischoff et al. |
| 9,930,980 B2 * | 4/2018 | Pau .................. A47G 23/16 |
| 2014/0311239 A1 | 10/2014 | Marjanovic et al. |
| 2016/0137483 A1 * | 5/2016 | Pfeiffer ............. G01F 13/006 |
| | | 600/509 |
| 2017/0067770 A1 * | 3/2017 | Sun .................. G01F 15/063 |
| 2018/0197629 A1 * | 7/2018 | Zhou ................. G16H 40/63 |
| 2019/0015299 A1 * | 1/2019 | Pyka .................. A61J 9/063 |
| 2019/0125630 A1 * | 5/2019 | Van Kollenburg ....... A61J 9/06 |

OTHER PUBLICATIONS

Item 1: Baby Gigl Baby Gigl Description: Tracks baby bottle formula consumption with the correct bottle angle during feeding Website: http://www.slowcontrol.com/en/baby-gigl/ See attached Addendum: Non-Patent Literature for screen shots.

Item 2: Sleevely Sleevely Description: Tracks baby bottle formula consumption Website: http://sleevely.net/sleevely/ See attached Addendum: Non-Patent Literature for screen shots.

* cited by examiner

BABY BOTTLE SENSOR WITH CONTENT VOLUME SENSING AND CONTENT DEDUCTION LOGIC

RELATED APPLICATIONS

This is the first application filed for this invention.

FIELD OF THE INVENTION

This invention relates in general to nursing bottles for infants and, in particular, to a baby bottle sensor with content volume sensing and content deduction logic.

BACKGROUND OF THE INVENTION

Many infants require bottle feeding because they cannot be breastfed, they require supplemental nutrition, they are cared for by a caretaker who may feed them mother's milk or formula, or it is dictated by parental choice. Consequently, numerous designs and configurations for baby bottles have been invented. Recently, so-called "smart bottles" have been invented. One type of smart bottles has an integrated volume sensor designed to measure and record a volume of fluid consumed from the bottle, and report it to a wirelessly connected device. However, bottles with integrated volume sensors are expensive because every bottle requires a sensor and a control circuit to drive the sensor, etc. Certain other smart bottle devices having similar functionality are constructed as sleeves that receive a baby bottle and retain the bottle in a friction grip. Some even have orientation sensors to advise a user when the bottle is not supported at a proper angle for feeding a baby.

However, there is no known evidence of a smart bottle adapted to perform bottle content deduction. Bottle content deduction is desirable because parents like to know what their babies are being fed at any particular time when the baby is with a caregiver at home or at daycare. There therefore exists a need for a baby bottle and sensor with content volume sensing and content deduction logic that overcomes the shortcomings associated with the prior art.

SUMMARY OF THE INVENTION

It is therefore an object of the invention to provide a baby bottle sensor with content volume sensing and content deduction logic.

The invention therefore provides a baby bottle sensor with content volume sensing and content deduction logic, comprising in combination: a volume sensor to determine a volume of fluid in a baby bottle attached to the baby bottle sensor when the baby bottle is in an upright position; a motion sensor adapted to determine an orientation of the baby bottle sensor with respect to a horizon, and to detect motion of the baby bottle sensor in real time; and a central processing unit that executes program instructions to: receive signals from the motion sensor and further adapted to analyze the received signals to determine whether movements indicative of a mixing action for mixing formula powder with water in the baby bottle occurs prior to receiving signals indicative of a feeding of the baby from the baby bottle; deduce from the received signals whether formula that requires mixing, or some fluid that does not require mixing is contained in the baby bottle; and record the deduction in an electronic bottle record associated with the baby bottle.

The invention further provides a baby bottle sensor with content volume sensing and content deduction logic, comprising in combination: a capacitive sensing system that senses a volume of fluid in a baby bottle attached to the baby bottle sensor when the baby bottle is in an upright position; a motion sensor adapted to determine an orientation of the baby bottle sensor with respect to a horizon, and to detect motion of the baby bottle sensor in real time; and a central processing unit that executes program instructions to: receive signals from the motion sensor and further adapted to analyze the received signals to determine whether movements indicative of a mixing action for mixing formula powder with water in the baby bottle occurs prior to receiving signals indicative of a feeding of the baby from the baby bottle; deduce from the received signals whether formula that requires mixing, or some fluid that does not require mixing is contained in the baby bottle; and record the deduction in an electronic bottle record associated with the baby bottle.

The invention yet further provides a baby bottle sensor with content volume sensing and content deduction logic, comprising in combination: a baby bottle sensor base upon which a baby bottle attached to the baby bottle sensor rests; a capacitive sensing system with a capacitive sensor and a capacitive ground respectively housed in opposed elongated upright arms connected to the base and closely contacting opposite sides of the baby bottle, the capacitive sensing system being adapted to sense a volume of fluid in the baby bottle attached to the baby bottle sensor when the baby bottle is in an upright position; a motion sensing system that includes a digital accelerometer and a digital gyroscope, the motion sensing system being adapted to generate signals analyzed by a central processing unit to determine an orientation of the baby bottle sensor with respect to a horizon, and detect motion of the baby bottle sensor in real time; and the central processing unit further adapted to execute program instructions to: receive signals from the motion sensor and further adapted to analyze the received signals to determine whether movements indicative of a mixing action for mixing formula powder with water in the baby bottle occurs prior to receiving signals indicative of a feeding of the baby from the baby bottle; deduce from the received signals whether formula that requires mixing, or some fluid that does not require mixing is contained in the baby bottle; and record the deduction in an electronic bottle record associated with the baby bottle; and a Bluetooth transceiver adapted to receive data from the central processing unit and communicate the data to a paired Bluetooth device that runs program instructions for receiving and processing the data and displaying the processed data in a user interface of the paired Bluetooth device.

BRIEF DESCRIPTION OF THE DRAWINGS

Having thus generally described the nature of the invention, reference will now be made to the accompanying drawings, in which:

FIG. 4b is a top plan view of the bottle portion of the baby bottle shown in FIG. 4a;

DETAILED DESCRIPTION OF THE PREFERRED EMBODIMENTS

The invention provides a baby bottle sensor with a content volume sensor and content deduction logic. The baby bottle sensor has a base with an opposed pair of upright arms that respectively contact opposite sides of a baby bottle. In some embodiments the baby bottle sensor positively locks to a bottom of a compatible baby bottle. In other embodiments, the upright arms of the sensor have a resilient, slip-resistant inner surface that grips the outer perimeter of a generic baby bottle to retain the bottle in the sensor. The sensor includes a control circuit and a Bluetooth communications module. The control circuit includes the content volume sensor that determines a volume of fluid contained in the baby bottle. The control circuit also includes a motion sensor that generates signals that are analyzed for indications that formula is being mixed in the bottle and/or a baby is being fed with the bottle. If mixing is detected, the control circuit deduces that the baby bottle contains baby formula. If no mixing is detected prior to feeding, the control circuit deduces that another fluid, such as breast milk, water or juice, is being fed to the infant.

Figure 1:
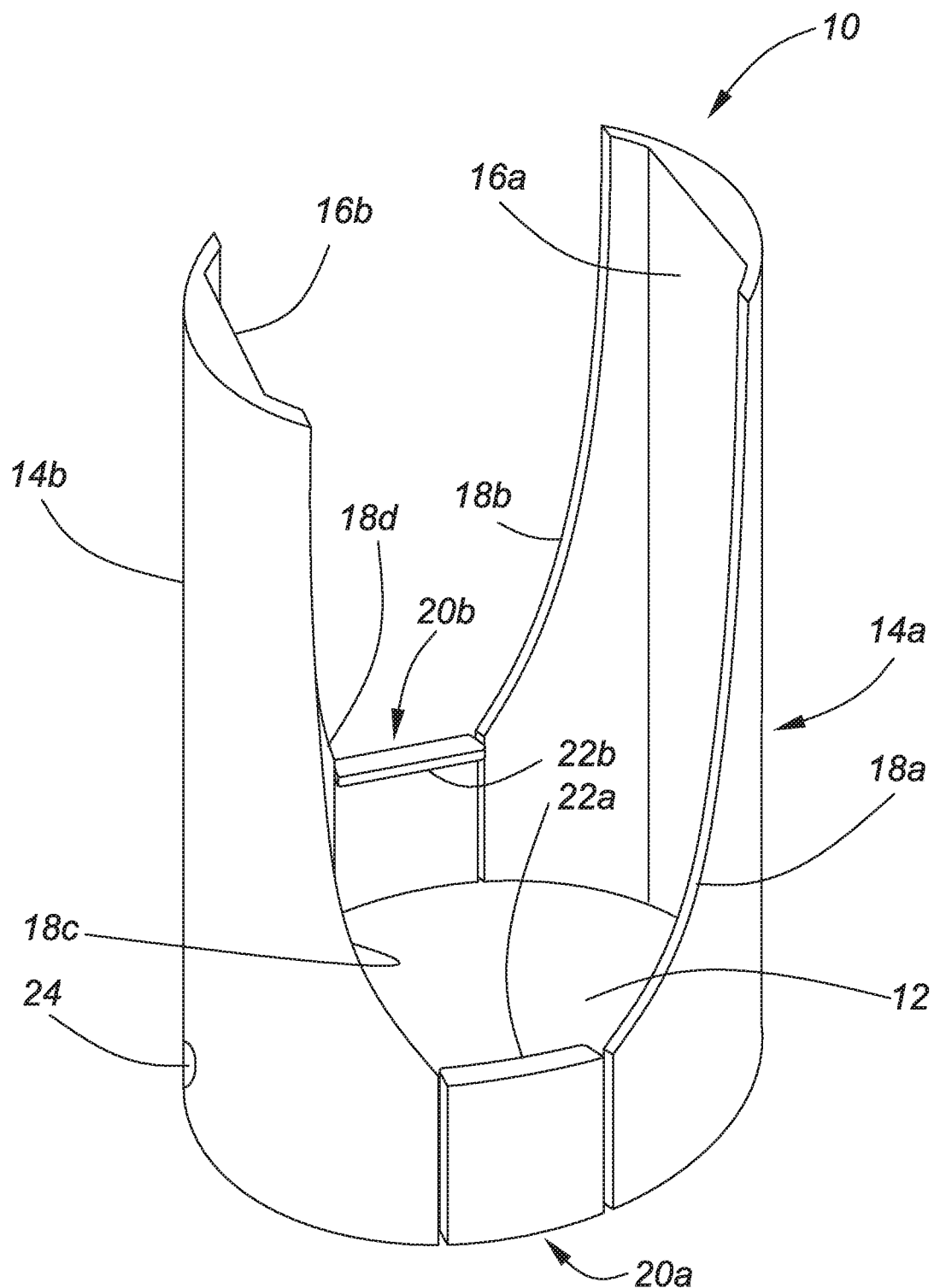
FIG. 1 is a perspective view of a sensor with volume sensing and content deduction logic in accordance with one embodiment of the invention.

FIG. 1 is a perspective view of one embodiment of a baby bottle sensor 10 (hereinafter simply "sensor 10") with volume sensing and content deduction logic in accordance with the invention. The sensor 10 has a base 12 that houses a control circuit and a Bluetooth communications module, as will be explained below in detail with reference to FIG. 15.

Figure 2:
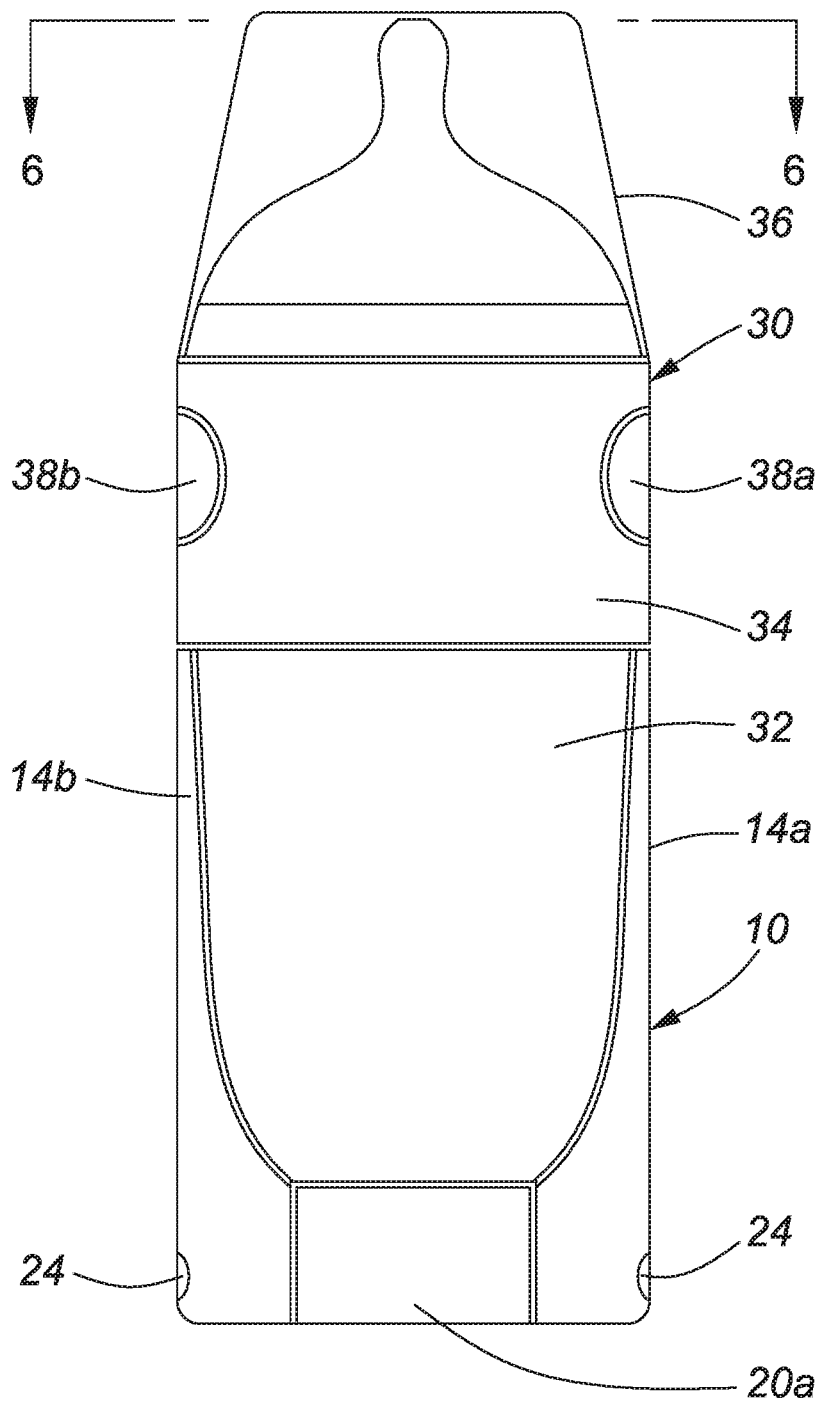
FIG. 2 is a front elevational view of a baby bottle attached to the sensor shown in FIG. 1.
Figure 3:
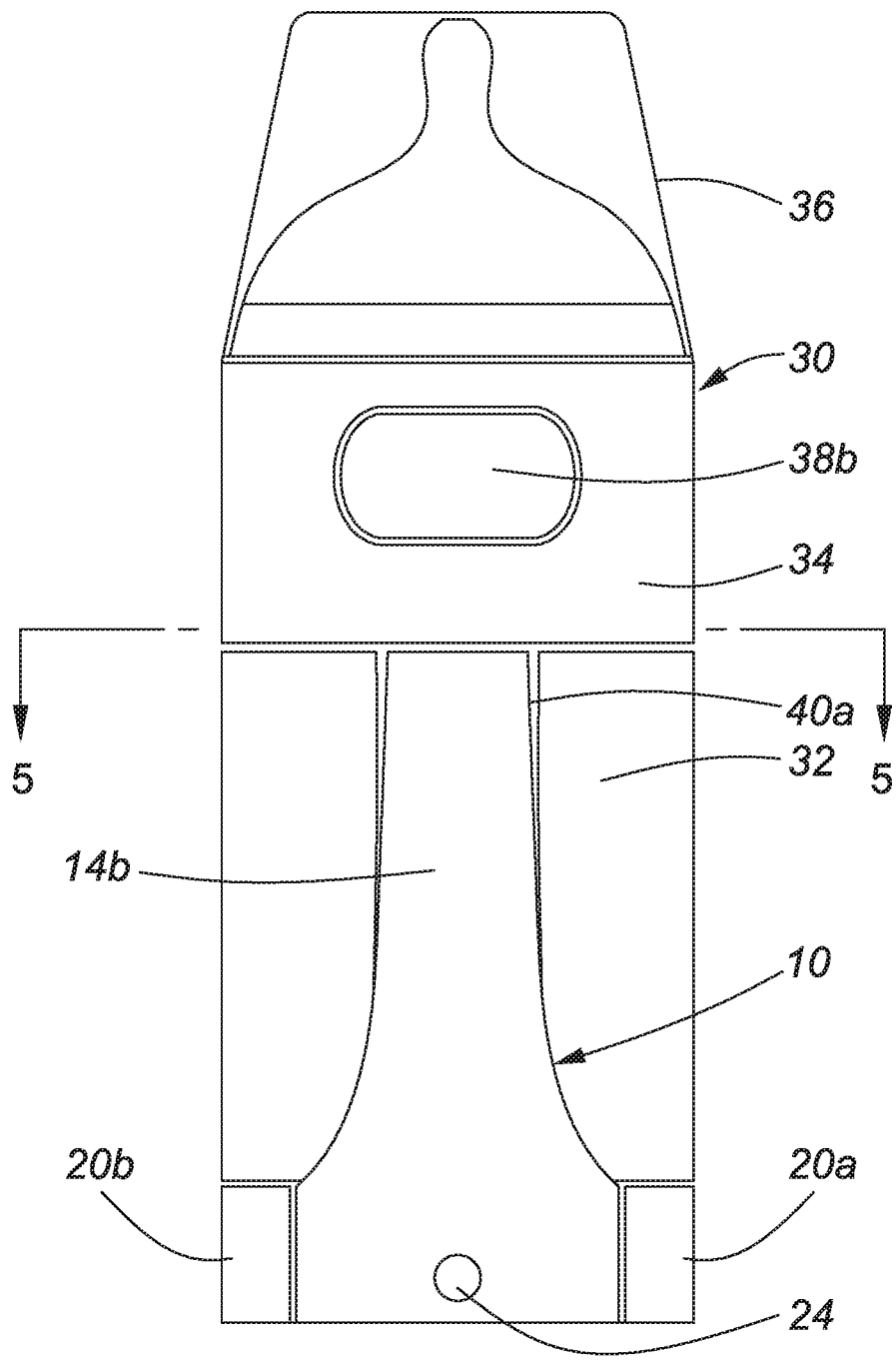
FIG. 3 is a side elevational view of the baby bottle with attached sensor shown in FIG. 2.

Integral with, or separately molded and affixed to, the base 12 are opposed upright arms 14a, 14b that closely contact opposite sides of a compatible baby bottle (see FIGS. 2 and 3). In this embodiment, each upright arm 14a, 14b has a flat inner surface 16a, 16b. The flat inner surfaces 16a, 16b mate with corresponding flat surfaces on the compatible baby bottle, as will be explained in more detail below with reference to FIGS. 3, 4 and 5. The upright arms 14a, 14b are at least partially hollow and respectively house one of an elongated capacitive sensor and an elongated capacitive ground of a capacitance sensing system, as will also be explained below in more detail with reference to FIG. 15. The shape of the upright arms 14a, 14b respectively provide space to accommodate the one of the capacitive sensor and the capacitive ground (see FIG. 15). The upright arms 14a, 14b may optionally house electronic noise shielding (not shown) to shield the capacitive sensor and the capacitive ground from extraneous electronic noise, as will be understood by those skilled in the art. In this embodiment, the respective upright arms 14a, 14b have robust inwardly curved side surfaces, 18a and 18b on upright arm 14a and 18c and 18d on upright arm 14b. The robust inwardly curved side surfaces lend rigidity and strength to the respective upright arms 14a, 14b. A pair of opposed, pivotally hinged lock buttons 20a, 20b are supported by the base 12 between the opposed upright arms 14a, 14b. An inner top edge of each lock button 20a, 20b includes an inwardly projecting lock tab 22a, 22b for locking the sensor 10 to a compatible baby bottle, as will be explained below in detail with reference to FIG. 5. In one embodiment, at least one of the upright arms 14a, 14b supports a light emitting diode (LED) 24 used to provide visual status signals to a user of the sensor, as will be explained below in more detail with reference to FIGS. 16a-16c. In one embodiment, the base 12, upright arms 14a, 14b and lock buttons 20a, 20b are injection molded in a manner well understood in the art using a thermoplastic such as a UV stabilized polyethylene, for example.

FIG. 2 is a front elevational view of one embodiment of the compatible baby bottle 30 with the sensor 10 shown in FIG. 1. The baby bottle 30 has many of the features described in Applicant's U.S. Pat. No. 9,580,227 which issued Feb. 28, 2017, the specification of which is incorporated herein in its entirety. As explained in Applicant's issued patent, the baby bottle includes a bottle portion 32, a collar portion 34, and a bottle cap 36. The collar portion 34 has integrated opposing seal plate release buttons 38a, 38b, the function of which is known, but explained below with reference to FIG. 6. A bottom end of the bottle portion 32 is molded to accommodate engagement of the lock tabs 22a, 22b (see FIG. 1) of lock buttons 20a-20b (only 20a can be seen in this view), as will be explained below in more detail with reference to FIG. 5.

FIG. 3 is a side elevational view of the baby bottle 30 with the sensor 10 shown in FIG. 2. As can be seen, the bottle portion 32 has opposed flat side surfaces 40a, 40b, only one, 40a, of which can be seen in this view. The flat side surfaces 40a, 40b will be explained in more detail below with reference to FIGS. 4a and 4b. The opposed flat side surfaces 40a, 40b mate with the corresponding flat surfaces 16a, 16b of the upright arms 14a, 14b of the sensor 10, described above with reference to FIG. 1.

Figure 4A:
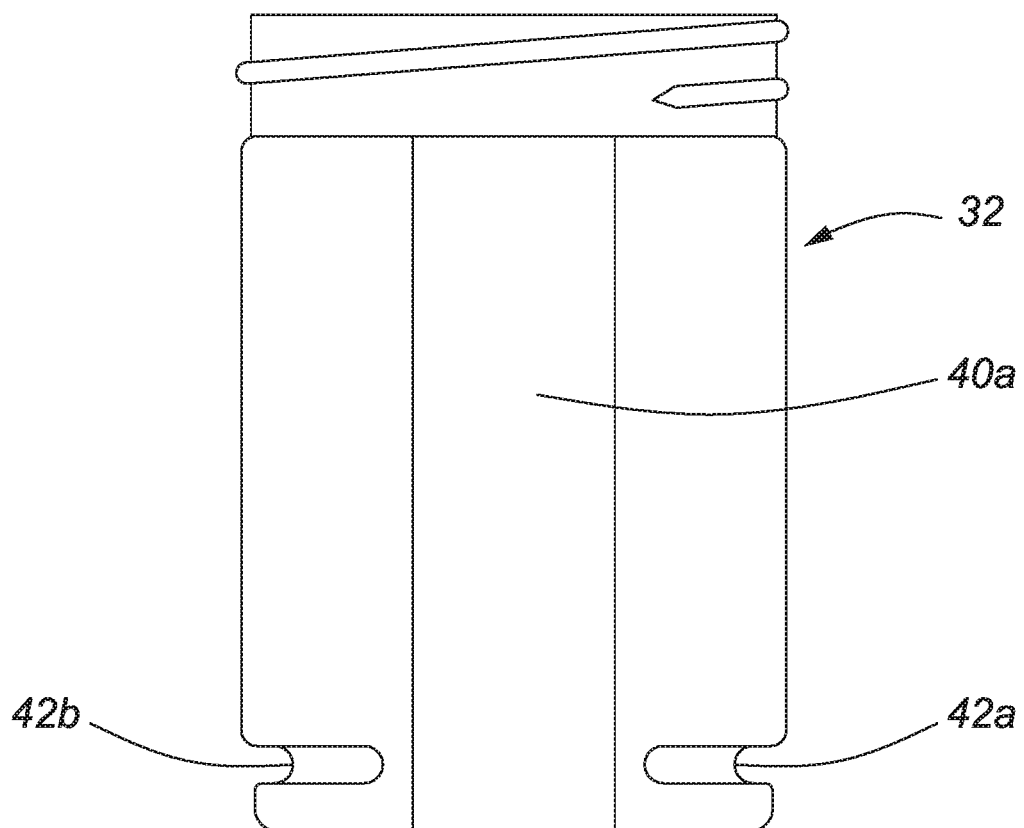
FIG. 4a is a side elevational view of the bottle portion of the baby bottle with attached sensor shown in FIGS. 2 and 3.

FIG. 4a is a side elevational view of the bottle portion 32 of the baby bottle 30 shown in FIGS. 2 and 3. As explained above, the bottom of the bottle portion 32 is molded with opposed grooves 42a, 42b to provide engagement for the lock tabs 22a, 22b shown in FIG. 1, which will be explained below in more detail with reference to FIG. 5.

Figure 4B:
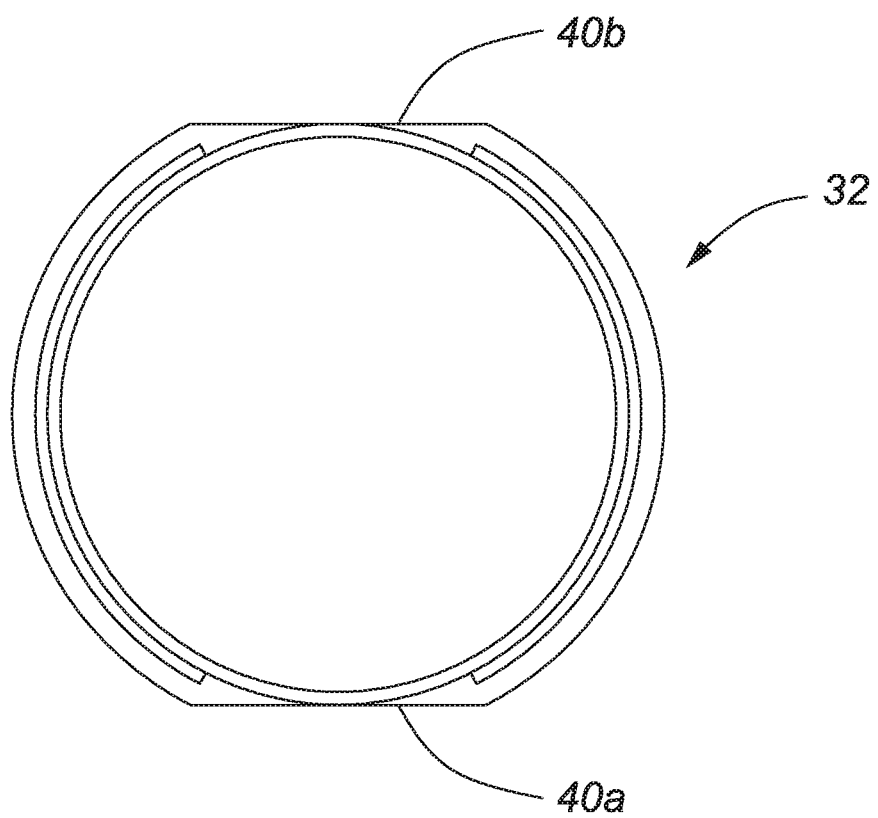

FIG. 4b is a top plan view of the bottle portion 32 of the baby bottle 30 shown in FIGS. 2 and 3. Both of the opposed flat side surfaces 40a, 40b of the bottle portion 32 can be seen.

Figure 5:
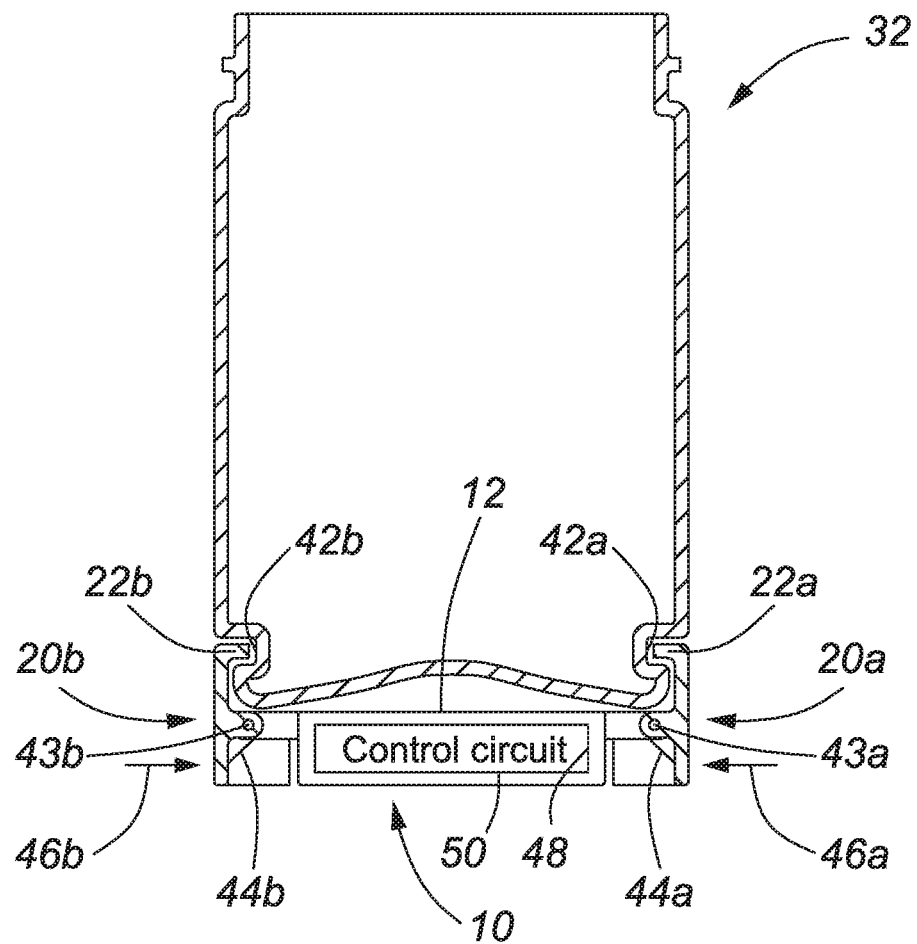
FIG. 5 is a cross-sectional view of the baby bottle portion and attached sensor taken along lines 5-5 of FIG. 3.

FIG. 5 is a cross-sectional view of the baby bottle portion 32 with sensor 10 taken along lines 5-5 of FIG. 3. The engagement of the respective lock tabs 22a, 22b of the respective lock buttons 20a, 20b in the respective opposed grooves 42a, 42b can be clearly seen. The lock buttons 20a, 20b are respectively pivotally hinged to the sensor base by respective hinge pins 43a, 43b, for example. Digital pressures 46a, 46b applied by a user against a bottom of the respective lock buttons 20a, 20b overcomes a resistive force of respective torsion springs 44a, 44b to rotate the respective lock tabs 22a, 22b out of the respective lock grooves 42a, 42b and release the baby bottle 30 from the sensor 10. The sensor base 12 includes a housing 48 that houses a control circuit 50, which will be explained below with reference to FIG. 15, as noted above. The housing 48. includes a fluid-sealed access port (not shown) to permit changing of a battery that powers the control circuit 50.

Figure 6:
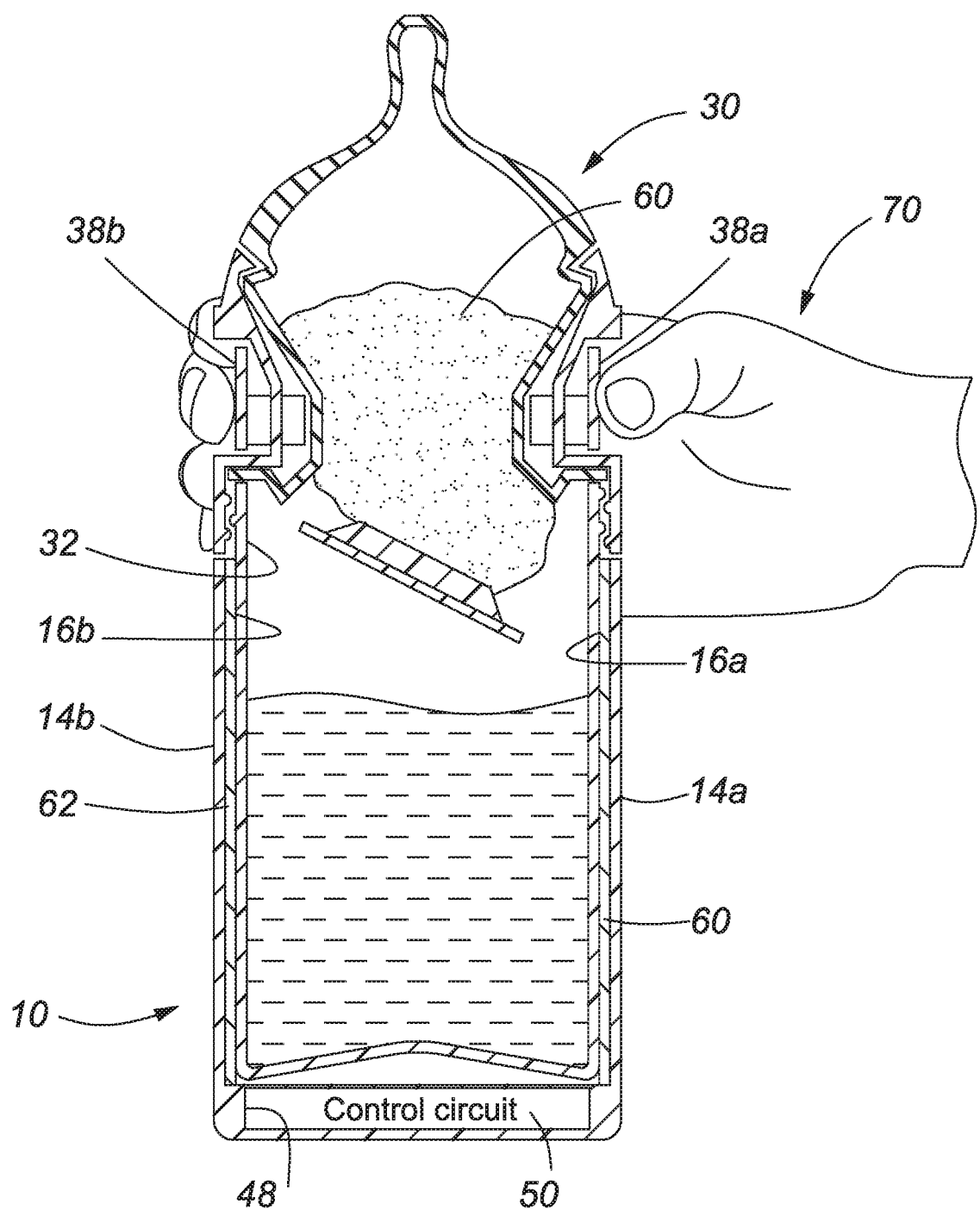
FIG. 6 is a cross-sectional view of the baby bottle and attached sensor taken along lines 6-6 of FIG. 2, showing the release of formula powder into the baby bottle.

FIG. 6 is a cross-sectional view of the baby bottle 30 with sensor 10 taken along lines 6-6 of FIG. 2, showing formula powder 60 being released from the baby bottle 30 by a user 70 pressing the opposed seal plate release buttons 38a, 38b, as described in Applicant's issued patent incorporated herein by reference. One of the upright arms 14a, 14b houses a capacitive sensor 60 and the other houses a capacitive ground 62 for sensing a fluid level in the bottle portion 32, as will be explained in more detail below with reference to FIG. 15. The capacitive sensor 60 and the capacitive ground 62 are respectively electrically connected to the control circuit 50 housed in the housing 48 of the sensor base 12.

Figure 7:
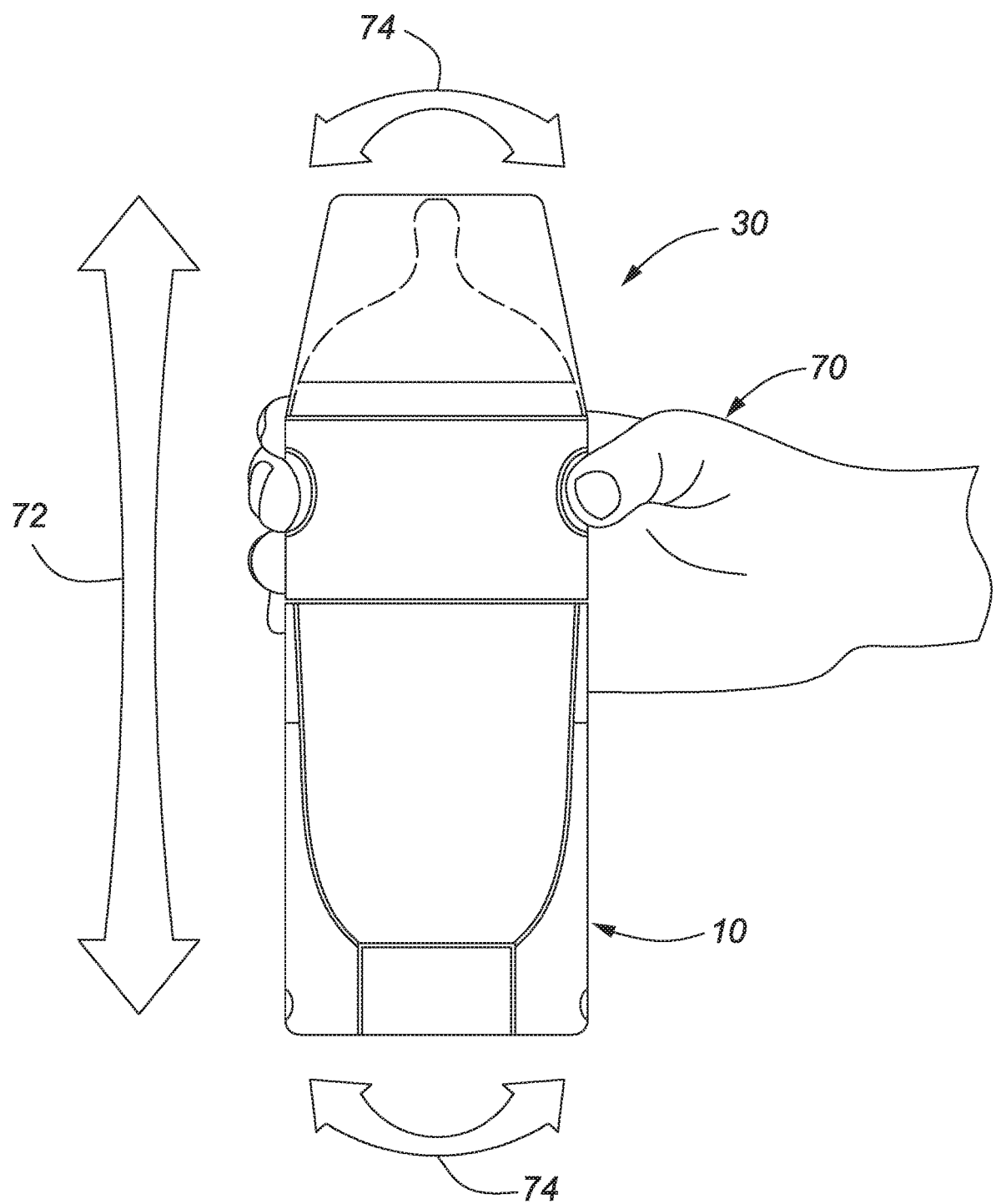
FIG. 7 is a schematic view of typical mixing actions following the release or addition of dry formula powder to a baby bottle shown, for example, in FIG. 6.
Figure 14:
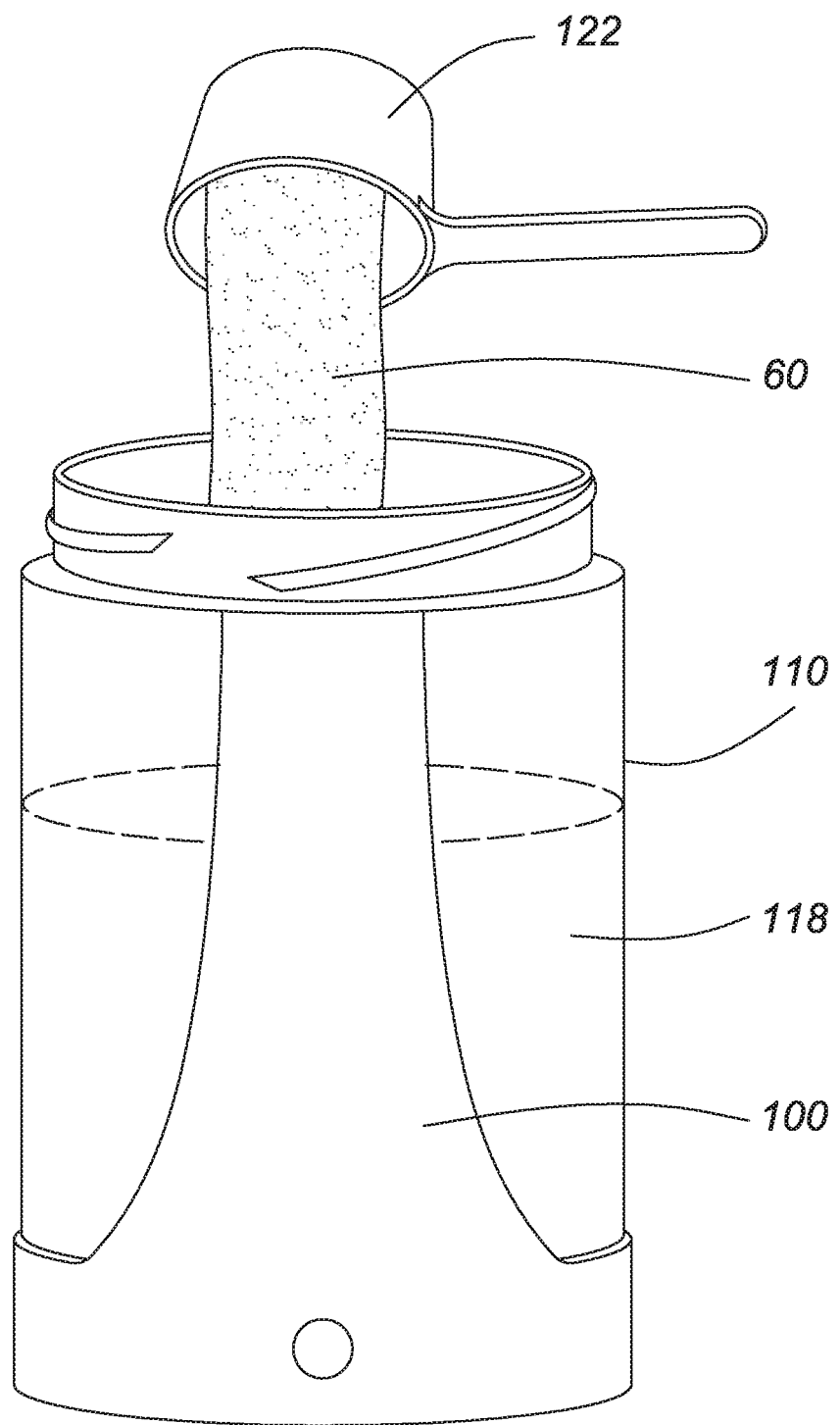
FIG. 14 is a side elevational view of the generic baby bottle inserted into the sensor shown in FIG. 12, showing the manual addition of formula powder to the generic baby bottle.

FIG. 7 is a schematic view of typical mixing actions following the release of the dry formula powder 60 shown in FIG. 6 or the addition of dry formula powder 60 shown in FIG. 14. It has been empirically determined that, in general, users 70 either mix formula with a pumping action 72, in which the bottle 30 with the sensor 10 is vigorously moved up and down in an arc by pivoting the forearm from the elbow, or in a side-to-side oscillation 74 by twisting the forearm. Both mixing actions work well, and each can be detected using appropriate electronic circuitry, as will be explained in more detail with reference to FIGS. 15 and 16a-c.

Figure 8:
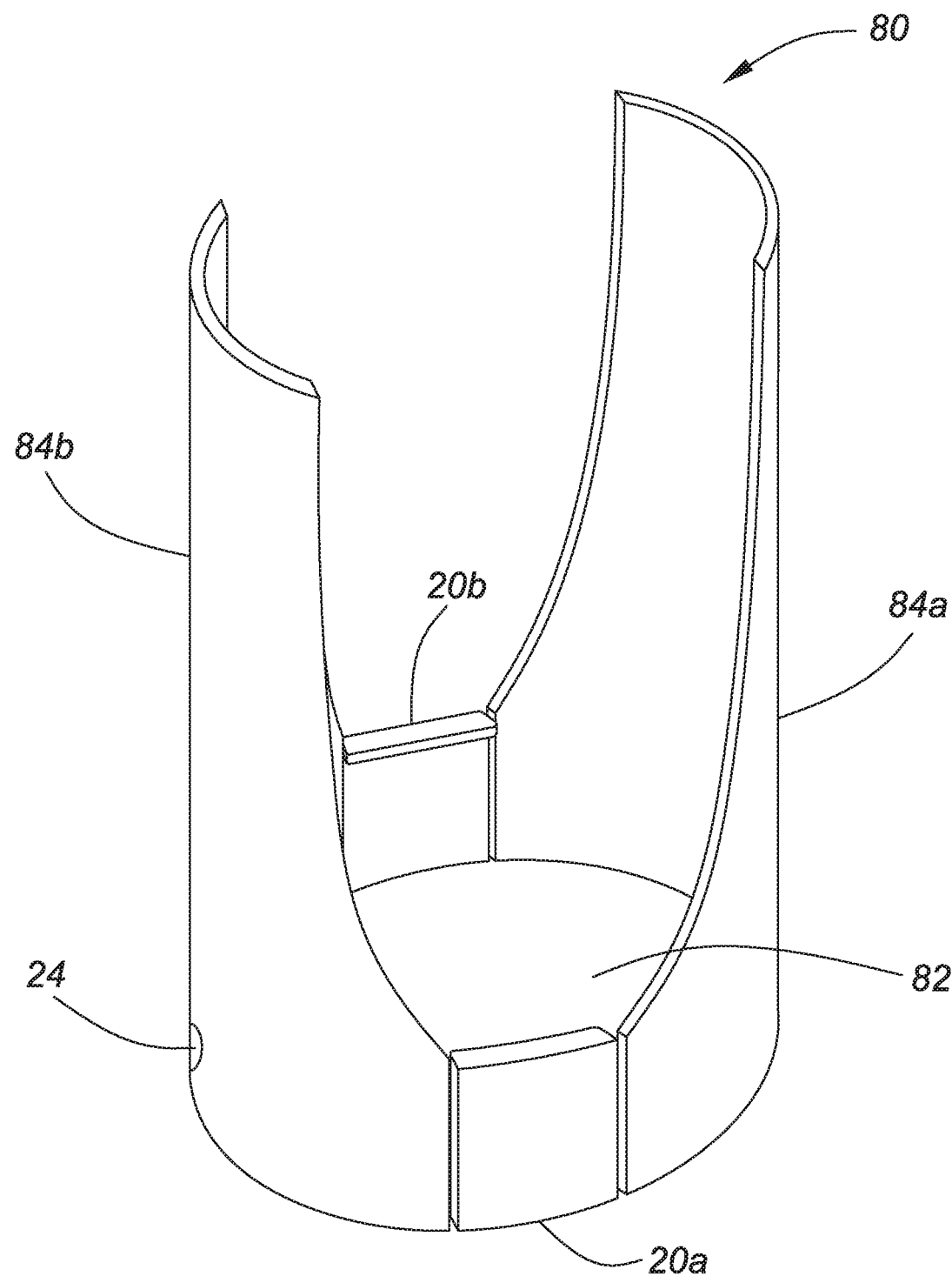
FIG. 8 is a perspective view of another embodiment of the sensor with volume sensing and content deduction logic in accordance with the invention.

FIG. 8 is a perspective view of another embodiment of a sensor 80 with volume sensing and content deduction logic in accordance with the invention. The sensor 80 is identical to the sensor 10 described above except that it is configured to accept a round bottle portion 92, best seen in FIG. 11. The sensor 80 has opposed upright arms 84a, 84b that respectively house one of a capacitive sensor and a capacitive ground. The capacitive sensor and the capacitive ground are shaped to accommodate the curved sidewalls of the upright arms 84a, 84b. The base 82 is identical to the base 12 described above except in the shape of a top surface thereof.

Figure 9:
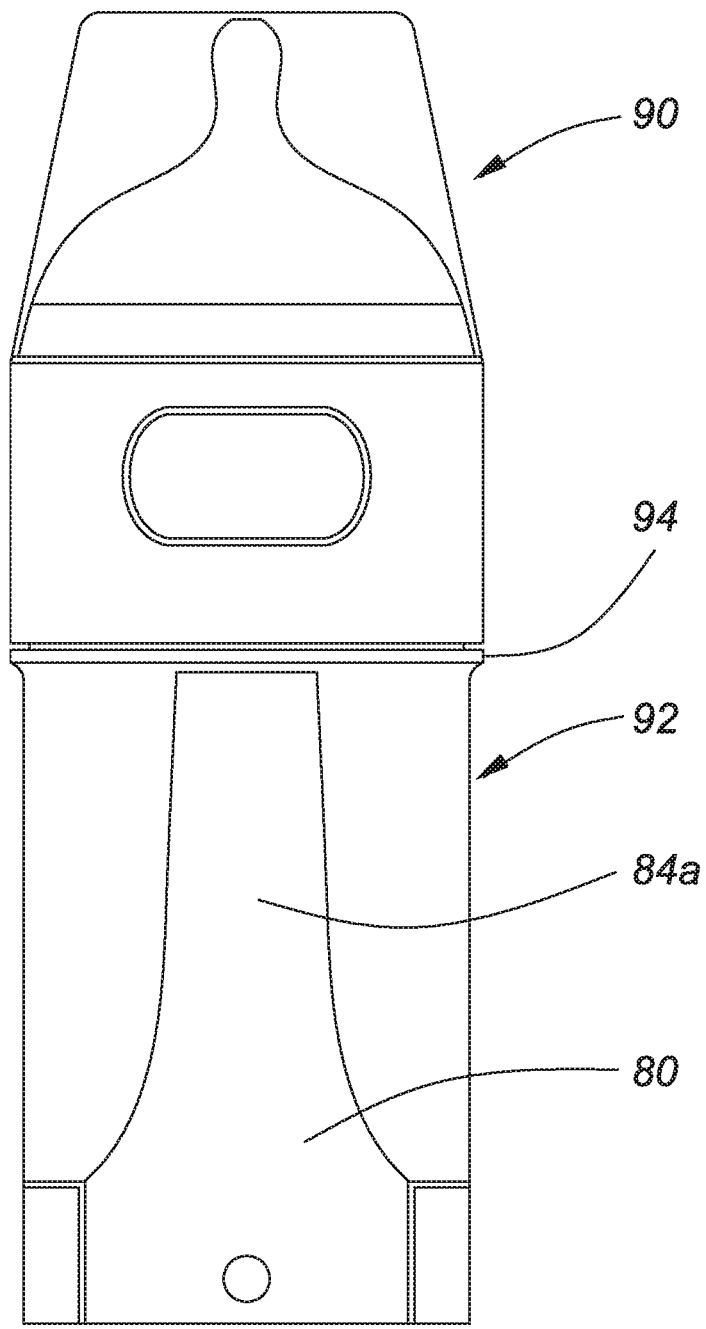
FIG. 9 is a side elevational view of another embodiment of a baby bottle attached to the sensor shown in FIG. 8.

FIG. 9 is a side elevational view of another embodiment of a baby bottle 90 attached to the sensor 80 shown in FIG. 8. The baby bottle 90 has a cylindrical bottle portion 92 with an outwardly curved top rim 94. In all other respects, the baby bottle 90 is identical to the baby bottle 30 described above, and will not be further described.

Figure 10:
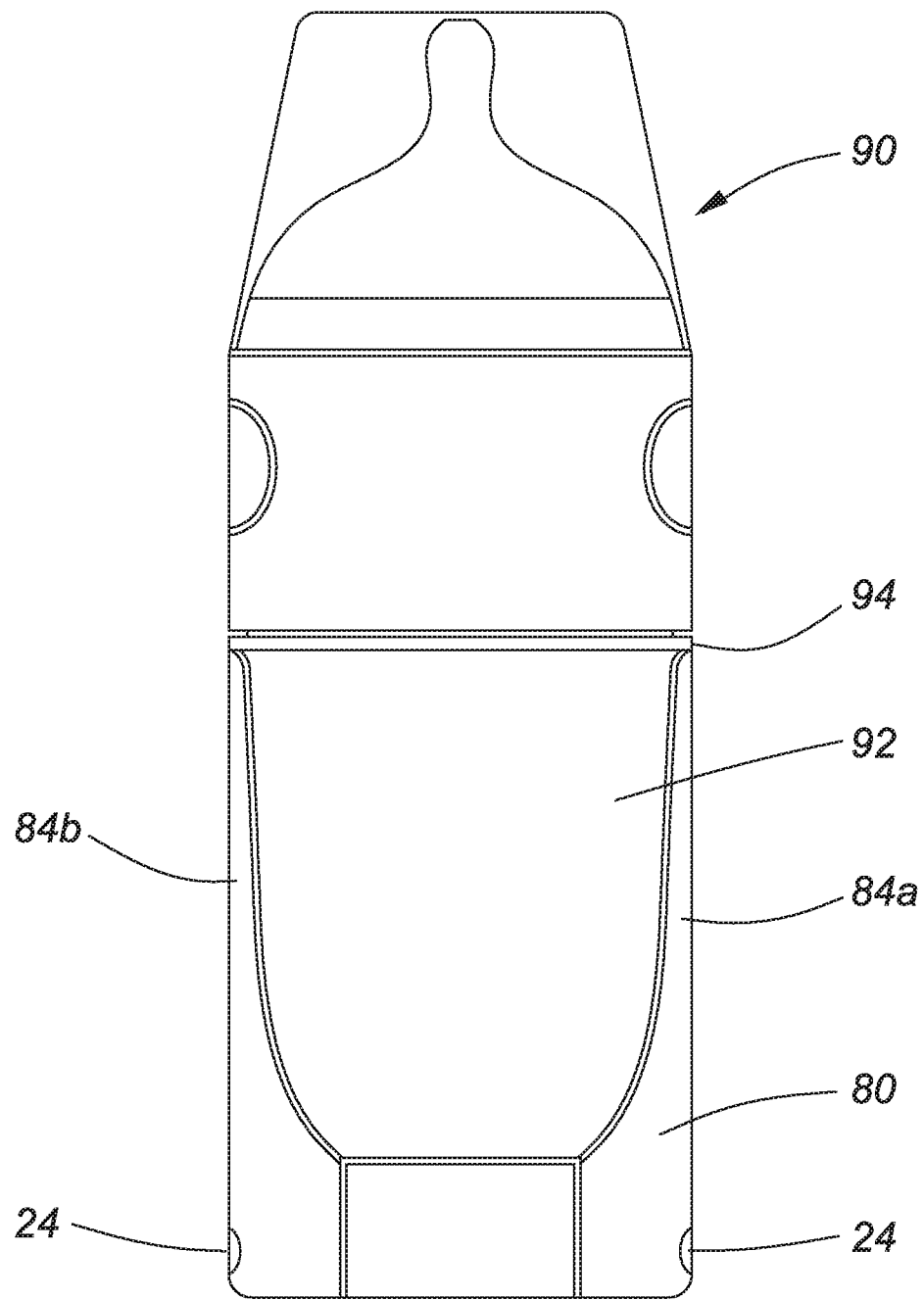
FIG. 10 is a front elevational view of the baby bottle with the attached sensor shown in FIG. 9.

FIG. 10 is a front elevational view of the baby bottle 90 with the attached sensor 80 shown in FIG. 9. As can be seen, on outer surface of the top rim 94 of the bottle portion 92 is flush with an outer surface of the upright arms 84a, 84b.

Figure 11:
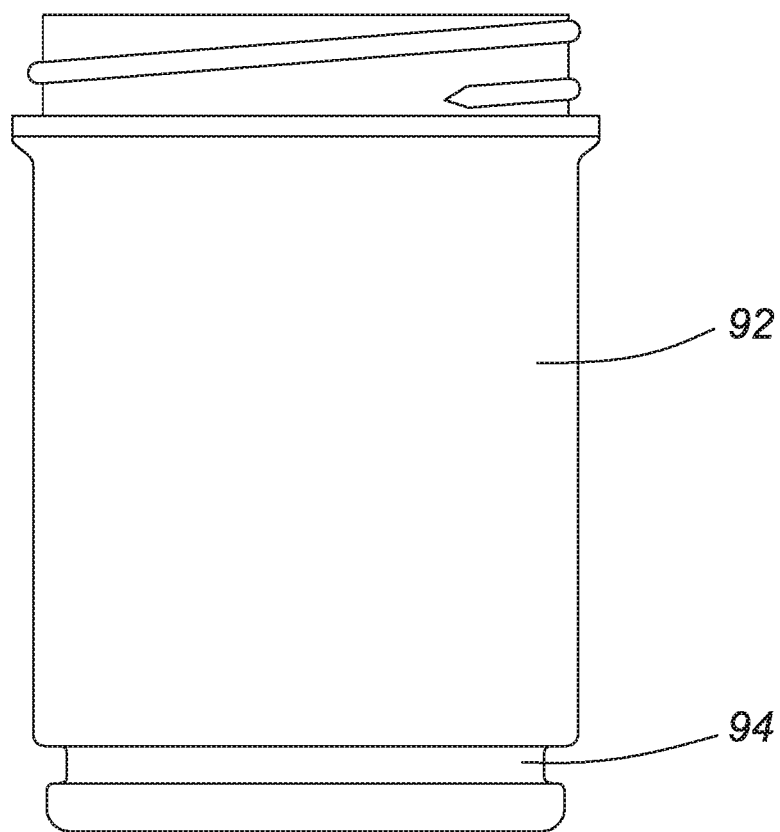
FIG. 11 is a side elevational view of the bottle portion of the baby bottle with the attached sensor shown in FIGS. 9 and 10.

FIG. 11 is a side elevational view of the bottle portion 92 of the baby bottle 90 shown in FIGS. 9 and 10. The cylindrical bottle portion 92 has an uninterrupted circumferential groove 94 around the bottom of the bottle portion 92.

Figure 12:
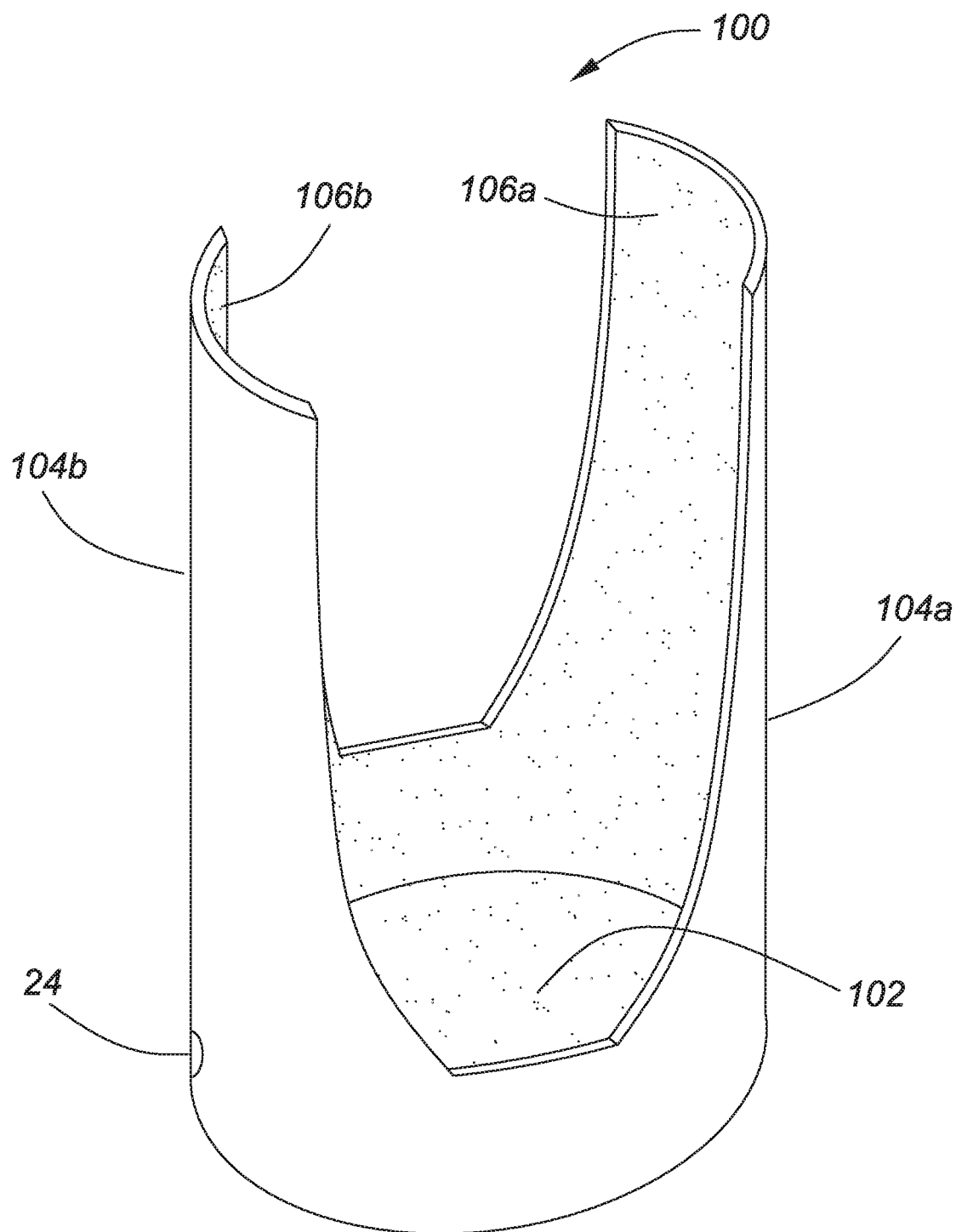
FIG. 12 is a perspective view of yet another embodiment of the sensor with content volume sensing and content deduction logic in accordance with the invention, for use with a generic baby bottle.

FIG. 12 is a perspective view of yet another embodiment of a baby bottle sensor 100 with content volume sensing and content deduction logic in accordance with the invention. The sensor 100 is designed for use with a generic baby bottle 110 (see FIG. 13), which is inserted between upright arms 104a, 104b of the sensor 100. The sensor 100 is identical to the sensor 80 described above, except that it is configured to secure the generic baby bottle 110 using a friction fit within the upright arms 104a, 104b of the sensor 100. The opposed upright arms 104a, 104b respectively house one of a capacitive sensor and a capacitive ground (see FIG. 15). The capacitive sensor and the capacitive ground are shaped to fit within the curved sidewalls of the upright arms 104a, 104b. Inside surfaces 106a, 106b of the upright arms 104a, 104b are provided with a surface texture that is frictionally adherent to both glass and plastic bottles so either bottle is held securely between the upright arms 104a, 104b until the bottle 110 is intentionally removed by lifting on the bottle 110 with one hand while holding down the sensor 100 with the other hand. The base 102 of the sensor 100 is identical to the base 82 described above in FIG. 8, except that it does not include opposed lock buttons.

Figure 13:
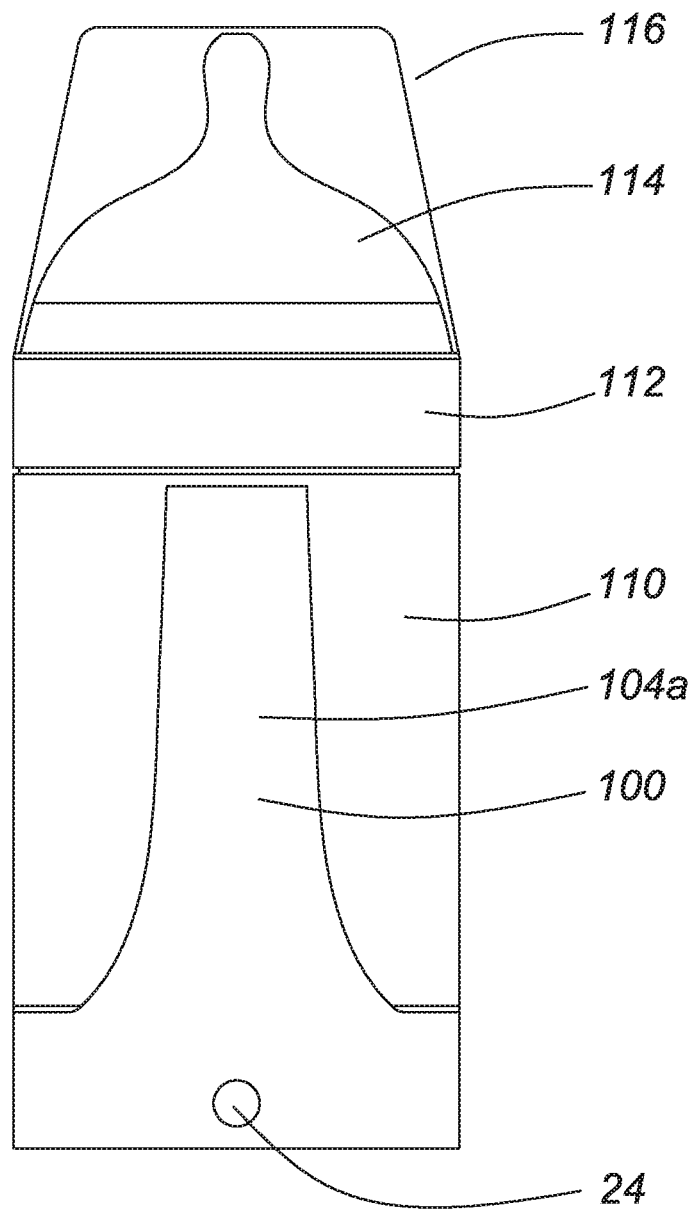
FIG. 13 is a side elevational view of a generic baby bottle inserted into the sensor shown in FIG. 12.

FIG. 13 is a side elevational view of the generic baby bottle 110 inserted into the sensor 100 shown in FIG. 12. As is well known in the art, the generic baby bottle 110 has a nipple ring 112 that connects a nipple 114 to the bottle 110. When not in use, the nipple 114 is covered by a removable cap 116. As explained above, the baby bottle 110 is held securely within the upright arms 104a, 104b (only 104a is visible in this view) of the sensor 100 by a friction fit between the bottle 110 and the respective sensor arms 104a, 104b.

FIG. 14 is a side elevational view of the generic baby bottle 110 inserted into the sensor 100 shown in FIG. 12 with the nipple ring and cap removed to permit the addition of formula powder 60. Formula power 60 must be manually added to the generic baby bottle 110 using a measuring scoop 122 provided by a manufacturer of the formula powder 60. After the formula powder 60 is added to the bottle 110 and the nipple ring is replaced, the bottle 110 is agitated by a user 70 employing one of the methods described above with reference to FIG. 7 to mix the formula powder 60 with water 118 in the bottle 110.

Figure 15:
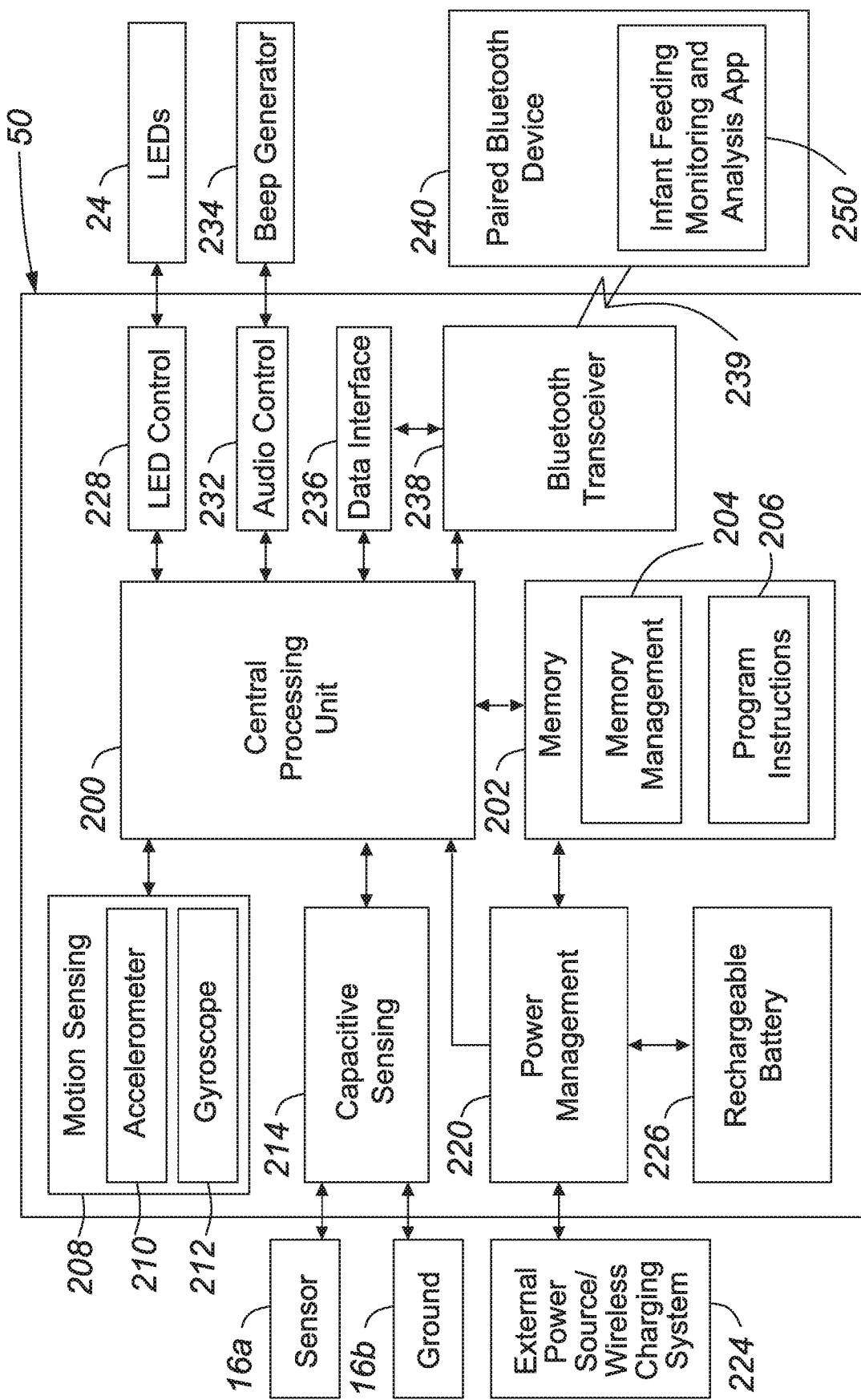
FIG. 15 is a schematic diagram of one embodiment of a control circuit for the sensors with content volume sensing and content deduction logic shown in FIG. 1, FIG. 8 and FIG. 12.

FIG. 15 is a schematic diagram of one embodiment of a control circuit 50 for the sensors 10, 80 and 100 with content volume sensing and content deduction logic shown respectively in FIG. 1, FIG. 8 and FIG. 12. It should be understood that the control circuit 50 can be realized in many different ways and will evolve over time as circuit implementation technology evolves. The control circuit 50 includes a central processing unit (CPU) 200 that monitors signals from all sensing systems and executes programmed instructions 206 to perform functions that will be described below in detail with reference to FIGS. 16a-c. The control circuit 50 further includes motion sensing 208 which in one embodiment includes a digital accelerometer 210 and a digital gyroscope 212, well known in the art. As described above, the control circuit 50 further includes the capacitive sensing system 214 connected to the CPU 200. The capacitive sensing system 214 is in turn electronically connected to the capacitive sensor 16*a* and capacitive ground 16*b*. As well understood in the art, the capacitive sensing system 214 includes resonant circuit drivers (not shown) that generate an electric drive frequency for the capacitive sensor 16*a* and the capacitive ground 16*b*. The control circuit 50 further includes power management 220. The power management 220 is provided with an interface for connection to an external power source and/or a wireless charging system 224, both of which are well known in the art. Power management is also provided with an interface with a rechargeable battery 226, which provides operating power to all components of the control circuit 50. A memory module 202, which may be integral with the CPU 200, includes memory management 204, program instructions 206 and data storage for data collected by the CPU 200 while executing the program instructions 206.

The control circuit 50 further includes control circuits to drive light emitting diode(s) and a sound generator, which may be respectively used alone or in unison to communicate with a user of the sensor 10. In one embodiment, the control circuit 50 includes a light emitting diode (LED) control 228 which drives LEDs 24 in a manner well known in the art, and audio control 232 that drives a beep generator 234, which may be implemented as a micro-speaker, for example. A data interface 236 receives selected data from the CPU 200 and passes it to a Bluetooth transceiver 238 when a Bluetooth connection 239 is established with a paired Bluetooth device 240. The paired Bluetooth device 240 executes programs instructions for receiving and processing the data and displaying the processed data in a user interface (not shown) of the paired Bluetooth device 240. In one embodiment, the program instructions executed by the paired Bluetooth device 240 are packaged in an Infant Feeding Monitoring and Analysis application 250 for the displaying information collected by the control circuit 50. The specifications for the Infant Feeding Monitoring and Analysis application 250 is beyond the scope of this disclosure, apart from a high-level description of the data that may be collected and communicated to the paired Bluetooth device 240, which is described below with reference to FIGS. 16*a-c*.

Figure 16A:
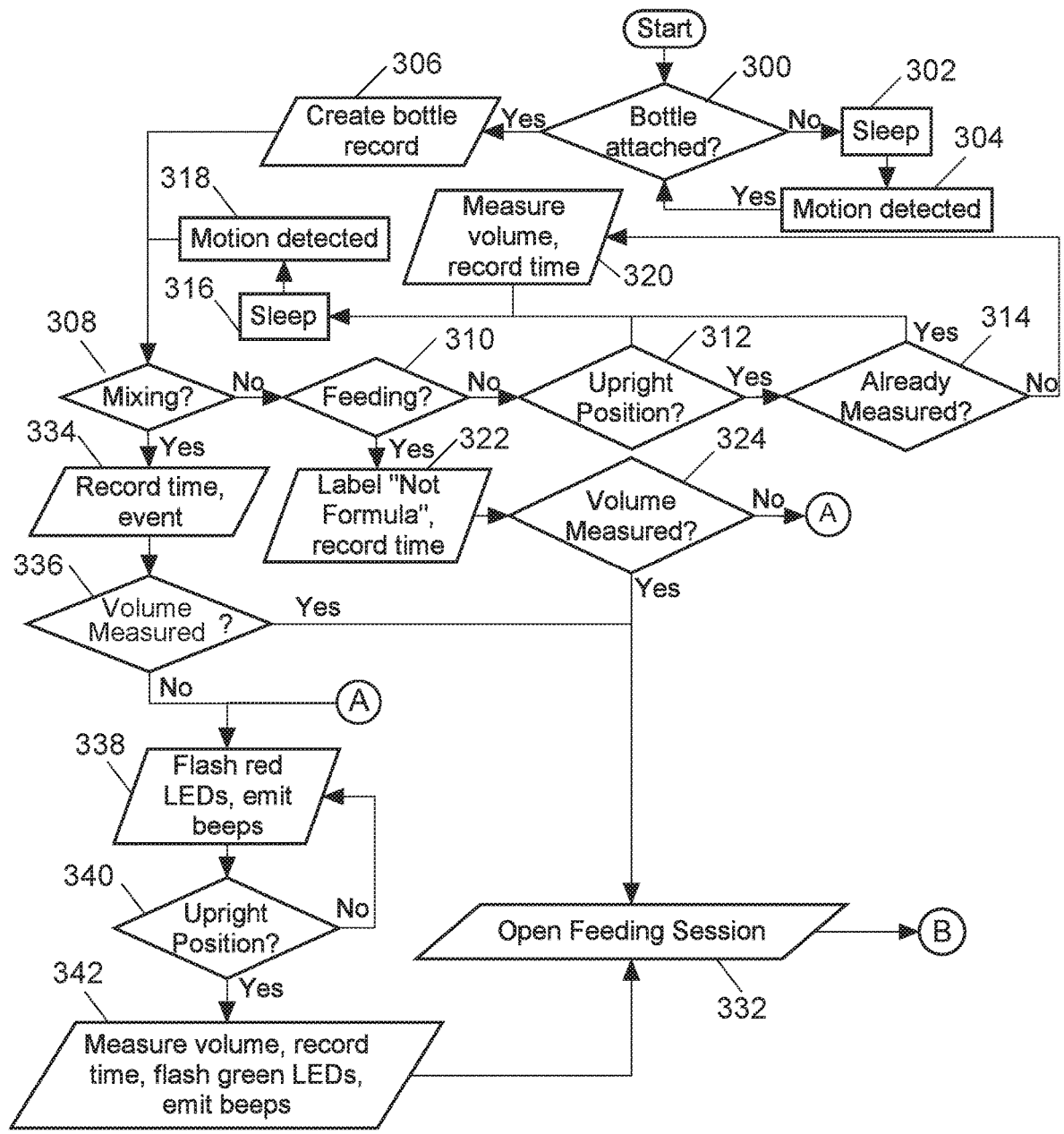
FIGS. 16a-16c are, collectively, a flow chart of one embodiment of logic executed by a central processing unit of the control circuit show in FIG. 15.
Figure 16B:
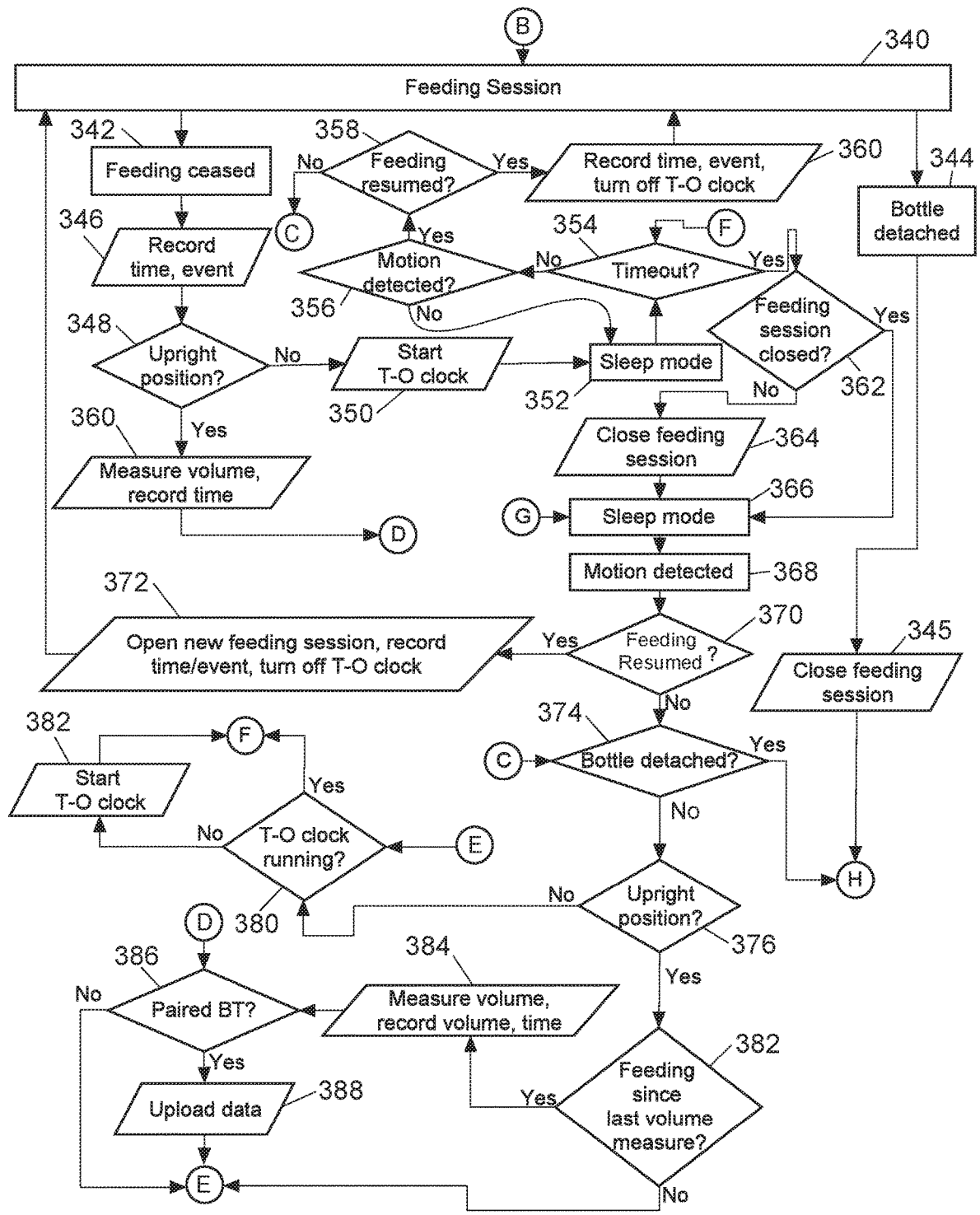
Figure 16C:
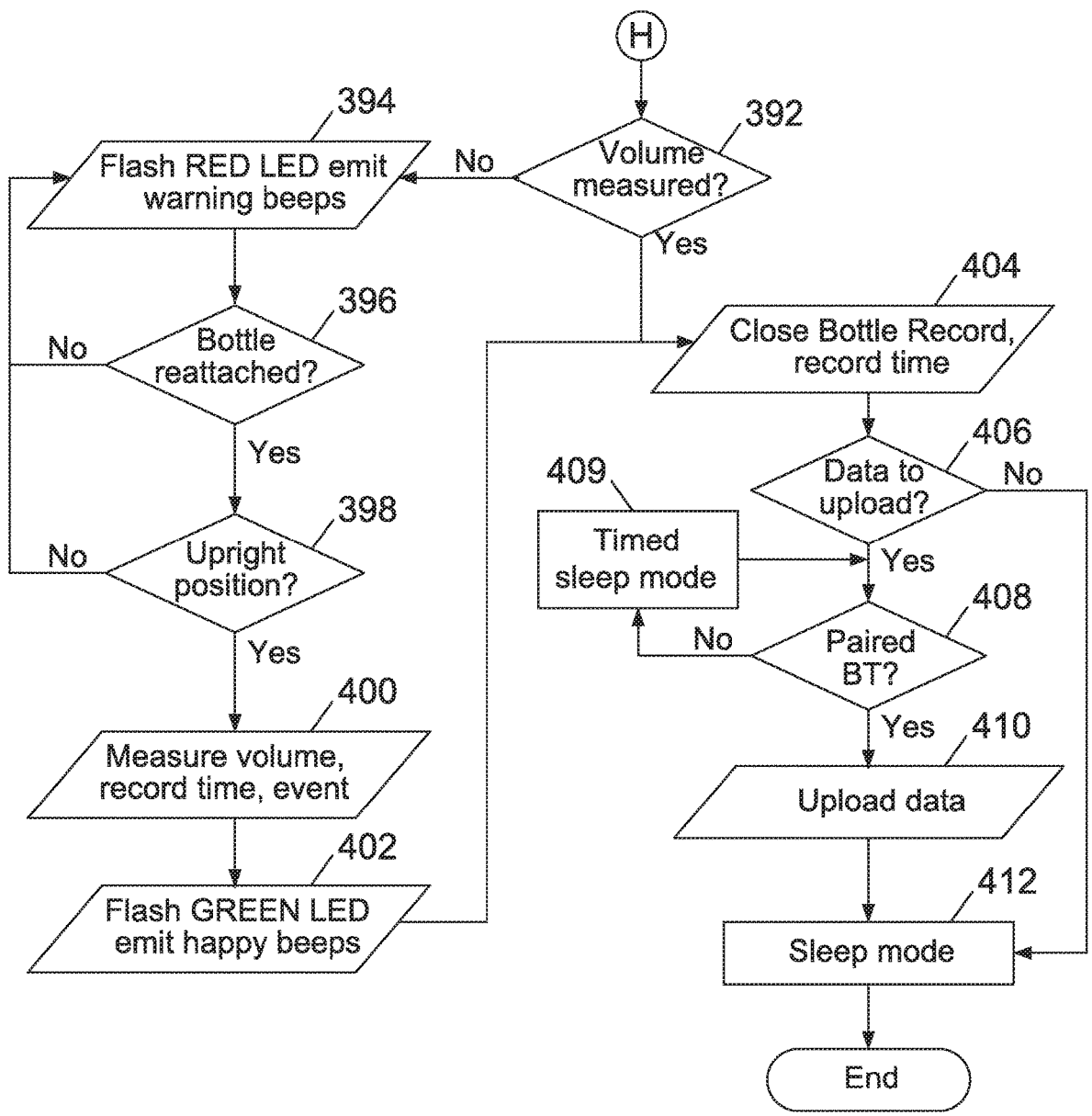

FIGS. 16*a*-16*c* are a flow chart of logic used by a central processing unit of the control circuit 50 show in FIG. 15. The CPU 200 operates most of the time in a low power "sleep" mode that only monitors signals from motion sensing 208. When movement of the sensor is detected, the CPU 200 first determines (at 300) if there is a bottle attached to the sensor 10, 80, 100 (hereinafter referred to simply as sensor 10). This is done by first checking the memory 202 (at 300) to determine if a "bottle record" already exists, which gives a positive indication that a bottle is attached to the sensor). The bottle record is a data record associated with and maintained for each bottle attached to the sensor 10. The bottle record is opened when the bottle is attached to the sensor 10, and closed when the bottle is detached from the sensor 10. If a bottle record does not exist, the CPU 200 queries (at 300) capacitive sensing 214 to determine if a bottle has been attached to the sensor 10. If there is no bottle attached to the sensor 10, the CPU 200 returns to the low power sleep state (at 302) until motion is again detected (at 304). When a bottle is first attached to the sensor 10, the CPU 200 creates the bottle record (at 306) with a unique identifier and stores the bottle record in the memory 202 (see FIG. 15). It then monitors motion sensing 208 for a predetermined period of time to determine (at 308) if movement indicating a mixing action is occurring. If the mixing action is not detected, motion sensing 208 is monitored (at 310) for a predetermined period of time to determine if the bottle is in a feeding orientation and feeding is occurring. Feeding from the bottle can be deduced by monitoring output from the accelerometer 210 to detect a rhythmic oscillation of bottle while the digital gyroscope 212 indicates that the baby bottle is at an inclination at which feeding is probable. If the bottle is not inclined at a feeding inclination, the CPU 200 monitors motion sensing 208 to determine (at 312) if the bottle is in an upright position. If the bottle is in an upright position, the CPU 200 determines whether a fluid volume of the bottle has already been measured (at 314). If the fluid volume has not already been measured, capacitive sensing 214 is activated to measure the volume of fluid contained in the bottle (at 320) and the volume is recorded in the bottle record along with a current time stamp. The CPU 200 then resumes the low power sleep state (at 316) until motion is once more detected (at 318).

If feeding was detected at 310, without detecting a mixing operation at 308, the CPU 200 deduces that something other than formula (breast milk for example) is being fed and the bottle record is updated (at 322) with a current time stamp and an indication that a fluid that is not formula is being fed. Immediately thereafter, the CPU 200 determines (at 324) if a pre-feeding fluid volume in the bottle has been measured. If not, the CPU 200 executes program instructions (at 338) to send signals to LED control 228 to flash a red LED(s) and program instructions to audio control 232 to emit "unhappy" beeps that are audible to the user 70 until motion sensing 208 indicates (at 340) that the bottle is supported in a stable upright position so the fluid volume can be measured. Once the pre-feeding fluid volume has been measured, the CPU 200 updates the bottle record with the pre-feeding volume and a time stamp (at 342) and executes program instructions to signal LED control 228 to flash green LED(s) and signal audio control 232 to generate "happy" beeps. A feeding session is then opened (at 332) and monitoring continues, as will be explained below with reference to FIG. 16*b*.

If mixing was detected (at 308), the time and the event are recorded (at 334) in the bottle record. If the user 70 puts the sensor 10, on a bottle immediately prior to mixing the formula, the volume of the fluid in the bottle will be unknown. Therefore, it is determined (at 336) if the fluid volume has been measured after the mixing action has ceased. If the fluid volume is known, a feeding session is opened (at 332). If not, the CPU 200 executes program instructions to send signals to LED control 228 to flash a red LED(s) and program instructions to send signals to audio control 232 to emit "unhappy" beeps that are audible to the user 70 (at 338) until the bottle is supported in a stable upright position (determined at 340) so the pre-feeding fluid volume can be measured. Once the pre-feeding fluid volume has been measured using capacitive sensing 214, the CPU 200 updates (at 342) the bottle record with the pre-feeding fluid volume and a current time stamp, executes program instructions to signal LED control 228 to flash green LED (s), and executes program instructions to signal audio control 232 to generate "happy" beeps. A feeding session 332 is then opened (at 332) and monitoring for motion continues, as will be explained below with reference to FIG. 16*b*.

Anyone familiar with feeding babies understands that feeding the contents of a bottle to a baby may or may not be a continuous process. The baby may be distracted, fall asleep for a while, become disinterested and want to rest or play for some time before resuming their feeding, or for any number of reasons unrelated to the baby itself. In order to provide coherent and comprehensible data to a parent, the concept of a "feeding session" is used to agglomerate feeding data. A feeding session, as explained below, once opened remains open until: a) the bottle is detached from the sensor 10; or b) feeding ceases for the duration of a predetermined timeout period. More than one feeding session may be associated with a bottle record, as will be described below.

FIG. 16b provides a high-level symbolic overview of program instructions executed by the CPU 200 during a feeding session. The CPU 200 executes program instructions to analyze signals from motion sensing 208 during the feeding session (at 340) to determine whether the infant is continuing to drink fluid from the bottle. As described above, feeding is detected by determining an inclination of the bottle with respect to a horizon, and a rhythmic oscillation of the bottle as the baby sucks on the nipple. If feeding stops and the capacitive sensing 214 indicates that the sensor 10 has been removed from the bottle (at 344), the feeding session is closed (at 345) and the CPU 200 executes programed instructions for a post bottle detachment process, as will be described below with reference to FIG. 16c. If it is determined that feeding has ceased (at 342) but the bottle has not been detached, the CPU 200 executes program instructions to update the bottle record with the event and a time stamp (at 346). The CPU 200 then executes program instructions to analyze signals from motion sensing 208 to determine if the bottle has been placed in an upright position (at 348). If so, the CPU 200 executes program instructions (at 360) to activate capacitive sensing 214 to measure the fluid volume in the bottle and record it in the bottle record along with a time stamp. The CPU then executes program instructions to activate the Bluetooth transceiver 238 to determine if there is a paired Bluetooth device 240 available (at 386). If a paired Bluetooth device 240 is available, the CPU executes program instructions to activate the data interface 236 to upload (at 388) any data not uploaded since a last time a paired Bluetooth device 240 was available. The CPU 200 then executes programed instructions to determine (at 380) if a timeout clock it maintains is running, and if not the timeout clock is started (at 382). The CPU 200 then executes programed instructions to check the timeout clock (at 354) to determine if the timeout clock has expired. If the CPU 200 determines that the timeout clock has expired (at 354), the CPU 200 executes programed instructions to determine if the feeding session is closed (at 362). If the feeding session has not been closed, the CPU 200 executes programed instructions to close the feeding session (at 364), enters low power sleep mode (at 366) and monitors motion sensing 208 (at 368) until motion is detected (at 368). When motion is detected (at 368), the CPU 200 executes programed instructions to monitor motion sensing 214 to determine if feeding has resumed (at 370). If it is determined that feeding has resumed, the CPU 200 executes programed instructions to open a new feeding session, record the event and time in the bottle record and turn off the timeout clock (at 372). The CPU 200 then executes program instructions to return to the feeding session (at 340).

If analysis of the signals output by motion sensing 208 does not indicate that feeding has resumed (at 370), the CPU 200 executes programed instructions to initiate capacitive sensing 214 to determine if the bottle has been detached (at 374). If the bottle has been detached, the CPU 200 executes programed instructions for the post bottle detachment process, as will be described below with reference to FIG. 16c. If it is determined (at 374) that the bottle has not been detached, the CPU 200 executes programed instructions to monitor motion sensing 208 to determine if the bottle is in an upright (volume measurable) position (at 376), if not the CPU 200 executes programed instructions that loop it back to sleep mode (at 366, via 380, 354, 362 and 364), as described above. However, if it is determined (at 376) that the bottle is in an upright position, the CPU 200 executes programed instructions to check the bottle record to determine if there has been feeding since a last fluid volume measure was taken (at 382). If not, the CPU 200 executes programed instructions to loop back to sleep mode (at 366), as described above. If it is determined (at 382) that there has been feeding since the last fluid volume measure, the CPU 200 executes programed instructions to measure the fluid volume of the bottle and record the volume in the bottle record, with a time stamp (at 384). The CPU 200 then executes programed instructions to activate the Bluetooth transceiver 238 to search for a paired Bluetooth device 240 (at 386). If a paired Bluetooth device 240 is found, data is uploaded (at 388) then the program instructions loop back to the low power sleep mode (at 366), as described above.

Returning back to the decision to determine if the bottle is in an upright position (at 348), if the bottle is not placed in a upright position after feeding ceases the CPU 200 executes programed instructions to start the timeout clock (at 350), enters the low power sleep mode (at 352) for a predetermined time period. The CPU 200 then executes program instructions to check the timeout clock to determine if it has expired (at 354). If the timeout clock has not expired and no further motion is detected (at 356), the CPU 200 returns to sleep mode for the predetermined period of time (at 352). If further motion is detected (at 356) the CPU 200 executes programed instructions to analyze signals from motion sensing 208 to determine if feeding has resumed (at 358). If it is determined that feeding has not resumed (at 358), then the CPU 200 executes programed instructions to determine if the bottle has been detached (at 374). If so, the programmed instructions branch to the post bottle detachment process, as will be described below with reference to FIG. 16c. If it is determined that the bottle has not been detached (at 374), the CPU 200 executes programed instructions to determine if the bottle is in an upright position (at 376) and either measures, records and reports, if possible, the fluid volume; or checks the timeout clock and loops back to low power sleep mode, all of which have been described above. However, if it is determined that feeding has resumed (at 358), the CPU 200 executes programed instructions (at 360) to record the event and store it in the bottle record along with a time stamp, then return to the feeding session (at 340).

FIG. 16c provides a high-level symbolic overview of program instructions executed by the CPU 200 in the post bottle detachment process after the bottle has been detached from the sensor 10, indicating that feeding from the bottle has terminated. After the CPU 200 determines, by analyzing signals generated by capacitive sensing 214, that the bottle has been detached, the CPU 200 executes programed instructions to determine (at 392) if a current fluid volume of the bottle is known by examining the bottle record. If the current fluid volume is not known, the CPU 200 executes programed instructions to instruct LED control 228 to flash red LED(s) and instructs audio control 232 to emit "unhappy" warning beeps (at 394). The red LED(s) are flashed and beeps emitted until the sensor 10, 80, 100 is reattached to the bottle (at 396) and placed in an upright position (at 398). Then the CPU 200 executes programed instructions to measure the fluid volume of the bottle (at 400) and executes programed instructions to instruct LED control 228 to flash green LED(s) and audio control 232 to emit "happy" beeps (at 402) to confirm the volume measurement. Then the CPU 200 executes programed instructions to record a closing time stamp in the bottle record and closes the bottle record (at 404). The CPU 220 then executes program instructions to determine if there is data that has not been uploaded (at 406). If all data was previously uploaded, the CPU 200 enters a low power sleep state (at 412). If there is remaining data to be uploaded, the CPU 200 executes program instructions to activate the Bluetooth transceiver 238 to search for a Bluetooth paired device 240 (at 408). If a Bluetooth paired device 240 is found, the CPU 200 executes program instructions to move the data to be uploaded to the data interface 236 and to upload the data (at 410) using the Bluetooth transceiver 238. The CPU 200 then enters low power sleep mode (412). If a paired Bluetooth device is not found (at 408), the CPU 200 executes program instructions to enter a low power timed sleep state (at 409) for a predetermined time before it wakes up to scan for a paired Bluetooth device 240 once more. If it is determined (back at 392) that the current fluid volume is already known, the CPU 200 executes program instructions to close the bottle record (404), see if there is data to upload (at 406), search for a paired Bluetooth device 240 (at 408), upload data, if required (at 410) and sleep (at 412), as described above.

Although the invention has been described with reference to various embodiments, the description provided and the embodiments shown are exemplary only. For example, the volume sensor may be a volume by weight sensor, or a volume by electromagnetic reflection sensor, or any other volume sensing technology, rather than the capacitive sensor system described.

The scope of the invention is therefore to be limited solely by the scope of the appended claims.

I claim:

1. A baby bottle sensor with content volume sensing and content deduction logic, comprising in combination:
    a volume sensor to determine a volume of fluid in a baby bottle attached to the baby bottle sensor when the baby bottle is in an upright position;
    a motion sensor adapted to determine an orientation of the baby bottle sensor with respect to a horizon, and to detect motion of the baby bottle sensor in real time; and
    a central processing unit that executes program instructions to:
        receive signals from the motion sensor and further adapted to analyze the received signals to determine whether movements indicative of a mixing action for mixing formula powder with water in the baby bottle occurs prior to receiving signals indicative of a feeding of the baby from the baby bottle;
        deduce from the received signals whether formula that requires mixing, or some fluid that does not require mixing is contained in the baby bottle; and
        record the deduction in an electronic bottle record associated with the baby bottle.

2. The baby bottle sensor as claimed in claim 1 further comprising a data interface and a Bluetooth transceiver for communicating data accumulated in the bottle record to an external paired Bluetooth device.

3. The baby bottle sensor as claimed in claim 1 further comprising a control circuit to drive a light emitting diode used to communicate with a user of the baby bottle sensor.

4. The baby bottle sensor as claimed in claim 1 further comprising a control circuit to drive a sound generator used to communicate with a user of the baby bottle sensor.

5. The baby bottle sensor as claimed in claim 1 wherein the baby bottle sensor further comprises a pair of opposed elongated sensor arms that closely contact opposite sides of the baby bottle.

6. The baby bottle sensor as claimed in claim 1 wherein the volume sensor comprises a capacitive sensing system having a capacitive sensor and a capacitive ground connected to the capacitive sensing system, and the opposed elongated sensor arms respectively house a one of the capacitive sensor and the capacitive ground.

7. The baby bottle sensor as claimed in claim 1 the motion sensor comprises a digital gyroscope and a digital accelerometer.

8. The baby bottle sensor as claimed in claim 1 wherein the baby bottle sensor comprises a base with at least one lock button that locks the baby bottle sensor to a bottom of the baby bottle, the lock button being adapted to be moved by manual pressure to an unlocked condition for releasing the baby bottle from the baby bottle sensor.

9. The baby bottle sensor as claimed in claim 5 wherein an inside surface of the elongated sensor arms comprise a surface texture that is frictionally adherent to both glass and plastic baby bottles to securely hold the baby bottles between the upright arms.

10. A baby bottle sensor with content volume sensing and content deduction logic, comprising in combination:
    a capacitive sensing system that senses a volume of fluid in a baby bottle attached to the baby bottle sensor when the baby bottle is in an upright position;
    a motion sensor adapted to determine an orientation of the baby bottle sensor with respect to a horizon, and to detect motion of the baby bottle sensor in real time; and
    a central processing unit that executes program instructions to:
        receive signals from the motion sensor and further adapted to analyze the received signals to determine whether movements indicative of a mixing action for mixing formula powder with water in the baby bottle occurs prior to receiving signals indicative of a feeding of the baby from the baby bottle;
        deduce from the received signals whether formula that requires mixing, or some fluid that does not require mixing is contained in the baby bottle; and
        record the deduction in an electronic bottle record associated with the baby bottle.

11. The baby bottle sensor as claimed in claim 10 further comprising a Bluetooth transceiver for communicating data accumulated in the bottle record to an external paired Bluetooth device.

12. The baby bottle sensor as claimed in claim 10 further comprising a control circuit that drives a light emitting diode and a control circuit that drives a beep generator, used collectively or in unison, to communicate visual and/or auditory signals to a user of the baby bottle sensor.

13. The baby bottle sensor as claimed in claim 10 wherein the baby bottle sensor further comprises a pair of opposed elongated sensor arms that closely contact opposite sides of the baby bottle, the elongated sensor arms respectively housing one of a capacitive sensor and a capacitive ground connected to a capacitive sensing system.

14. The baby bottle sensor as claimed in claim 10 wherein the motion sensor comprises a digital gyroscope and a digital accelerometer that respectively generate signals analyzed by the central processing unit.

15. The baby bottle sensor as claimed in claim 10 wherein the baby bottle sensor comprises a base with at least one lock button that locks the baby bottle sensor to the baby bottle, the lock button comprising a lock tab that engages a groove in a bottom of the baby bottle, the lock button being pivotally hinged to a side of the baby bottle sensor so that it may be pivoted by manual pressure to be moved to an unlocked condition for releasing the baby bottle from the baby bottle sensor.

16. The baby bottle sensor as claimed in claim 10 wherein an inside surface of the elongated sensor arms comprise a surface texture that is frictionally adherent to both glass and plastic baby bottles to securely hold the respective glass and plastic baby bottles between the upright arms.

17. A baby bottle sensor with content volume sensing and content deduction logic, comprising in combination:
   a baby bottle sensor base upon which a baby bottle attached to the baby bottle sensor rests;
   a capacitive sensing system with a capacitive sensor and a capacitive ground respectively housed in opposed elongated upright arms connected to the base and closely contacting opposite sides of the baby bottle, the capacitive sensing system being adapted to sense a volume of fluid in the baby bottle attached to the baby bottle sensor when the baby bottle is in an upright position;
   a motion sensing system that includes a digital accelerometer and a digital gyroscope, the motion sensing system being adapted to generate signals analyzed by a central processing unit to determine an orientation of the baby bottle sensor with respect to a horizon, and detect motion of the baby bottle sensor in real time; and
   the central processing unit further adapted to execute program instructions to:
      receive signals from the motion sensor and further adapted to analyze the received signals to determine whether movements indicative of a mixing action for mixing formula powder with water in the baby bottle occurs prior to receiving signals indicative of a feeding of the baby from the baby bottle;
      deduce from the received signals whether formula that requires mixing, or some fluid that does not require mixing is contained in the baby bottle; and
      record the deduction in an electronic bottle record associated with the baby bottle; and
   a Bluetooth transceiver adapted to receive data from the central processing unit and communicate the data to a paired Bluetooth device that runs programs instructions for receiving and processing the data and displaying the processed data in a user interface of the paired Bluetooth device.

18. The baby bottle sensor as claimed in claim 17 wherein an inside surface of the elongated upright arms comprise a surface texture that is frictionally adherent to both glass and plastic baby bottles to securely hold the respective glass and plastic baby bottles between the upright arms when the baby bottle rests on the baby bottle sensor base.

19. The baby bottle sensor as claimed in claim 17 wherein the baby bottle sensor base comprises opposed lock buttons respectively located between the elongated upright arms, the opposed lock buttons comprising lock tabs that respectively engage a groove in a bottom of the baby bottle, the lock buttons being pivotally hinged to a side of the baby bottle sensor so that they may be pivoted by manual pressure to an unlocked condition for releasing the baby bottle from the baby bottle sensor.

20. The baby bottle sensor as claimed in claim 17 further comprising a power management circuit adapted to be connected directly or indirectly to an external power source, for recharging a rechargeable battery that provides operating power to the baby bottle sensor.

* * * * *